(12) United States Patent
Muyari et al.

(10) Patent No.: US 11,992,223 B2
(45) Date of Patent: May 28, 2024

(54) CLIP DEVICE

(71) Applicant: OLYMPUS CORPORATION, Hachioji (JP)

(72) Inventors: Yuta Muyari, Tokyo (JP); Tomohiro Tsuji, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/848,458

(22) Filed: Jun. 24, 2022

(65) Prior Publication Data

US 2022/0313268 A1 Oct. 6, 2022

Related U.S. Application Data

(63) Continuation of application No. 16/699,196, filed on Nov. 29, 2019, now Pat. No. 11,399,847, which is a (Continued)

(30) Foreign Application Priority Data

May 19, 2015 (JP) ................................. 2015-102117

(51) Int. Cl.
*A61B 17/128* (2006.01)
*A61B 17/122* (2006.01)
(Continued)

(52) U.S. Cl.
CPC ........ *A61B 17/1285* (2013.01); *A61B 17/122* (2013.01); *A61B 2017/2938* (2013.01); *A61B 2090/034* (2016.02)

(58) Field of Classification Search
CPC .......... A61B 2017/2938; A61B 17/122; A61B 2017/294; A61B 2017/2944;
(Continued)

(56) References Cited

U.S. PATENT DOCUMENTS

| 5,445,167 A | 8/1995 | Yoon et al. |
| 8,986,326 B2 | 3/2015 | Satake et al. |
| (Continued) | | |

FOREIGN PATENT DOCUMENTS

| EP | 2127606 A1 | 12/2009 |
| JP | 2002-191609 A | 7/2002 |
| (Continued) | | |

OTHER PUBLICATIONS

Mar. 16, 2018 Office Action issued in U.S. Appl. No. 15/490,334.
(Continued)

*Primary Examiner* — Brooke Labranche
*Assistant Examiner* — Lauren Dubose
(74) *Attorney, Agent, or Firm* — Oliff PLC

(57) ABSTRACT

A clip device includes a restraining tube having an insertion passage with a first arm part and a second arm part facing each other and disposed within the insertion passage and configured to protrude from the restraining tube. The clip device further includes an operation wire configured to move the first arm part. A first stopper is engaged to the first arm part and a second stopper is engaged to the second arm part. The first stopper is disposed in a region closer to a distal end of the restraining tube than the second stopper. The first stopper is configured to, in response to the operation wire moving from the distal end of the restraining tube to a proximal end of the restraining tube, move relative to the second stopper, contact the second stopper, and move in contact with the second stopper.

20 Claims, 14 Drawing Sheets

Related U.S. Application Data continuation of application No. 15/490,334, filed on Apr. 18, 2017, now Pat. No. 10,524,801, which is a continuation of application No. PCT/JP2016/064003, filed on May 11, 2016.

(51) Int. Cl.
*A61B 17/29* (2006.01)
*A61B 90/00* (2016.01)

(58) Field of Classification Search
CPC ..... A61B 17/128; A61B 17/12; A61B 17/083; A61B 2017/2926; A61B 2090/034; A61B 17/08; A61B 17/22031; A61B 2017/22035; A61B 2017/2902
See application file for complete search history.

(56) References Cited

U.S. PATENT DOCUMENTS

| | | | |
|---|---|---|---|
| 2002/0045909 A1 | 4/2002 | Kimura et al. | |
| 2006/0015531 A1 | 1/2006 | Fraind et al. | |
| 2006/0155310 A1* | 7/2006 | Binmoeller | A61B 17/122 606/151 |
| 2011/0112551 A1* | 5/2011 | Adams | A61B 17/083 606/142 |
| 2011/0184458 A1* | 7/2011 | Schurr | A61B 17/2909 606/205 |

FOREIGN PATENT DOCUMENTS

| | | |
|---|---|---|
| JP | 2004-073646 A | 3/2004 |
| JP | 2008-514244 A | 5/2008 |
| JP | 2010-178897 A | 8/2010 |
| JP | 2012-166003 A | 9/2012 |
| WO | 2006/028898 A2 | 3/2006 |

OTHER PUBLICATIONS

Jan. 21, 2019 Search Report issued in European Patent Application No. 16796358.6.
Mar. 22, 2019 Office Action issued in U.S. Appl. No. 15/490,334.
Jul. 19, 2016 Search Report issued in International Patent Application No. PCT/JP2016/064003.
Nov. 20, 2018 Office Action issued in U.S. Appl. No. 15/490,334.
Sep. 5, 2019 Notice of Allowance and Fee(s) Due issued in U.S. Appl. No. 15/490,334.
Jun. 18, 2021 Office Action Issued in U.S. Appl. No. 16/699,196.
Dec. 21, 2021 Office Action Issued in U.S. Appl. No. 16/699,196.
Mar. 24, 2022 Notice of Allowance issued in U.S. Appl. No. 16/699,196.
Aug. 2, 2016 Search Report issued in International Patent Application No. PCT/JP2016/064003.
Nov. 14, 2017 Office Action issued in U.S. Appl. No. 15/490,334.

* cited by examiner

CLIP DEVICE

CROSS REFERENCE TO RELATED APPLICATIONS

This application is a continuation application of U.S. patent application Ser. No. 16/699,196, filed Nov. 29, 2019, which is a continuation application of U.S. patent application Ser. No. 15/490,334, filed Apr. 18, 2017, which is a continuation application of International Patent Application No. PCT/JP2016/064003, filed May 11, 2016, which claims priority from Japanese Application No. 2015-102117, filed on May 19, 2015. The disclosures of the foregoing applications are hereby incorporated by reference in their entirety.

BACKGROUND

Technical Field

The claimed embodiments relate to a clip device that is inserted into a body and is used to ligate tissue.

Description of the Related Art

A clip device for ligating a target region using a clip for closure or hemostasis treatment of an opening occurring in biological tissue has been used for a long time. Such a clip device is inserted into a body using an endoscopic device. For example, a ligation device in which a clip part having a plurality of arms coupled to an operation wire is pulled into a pipe member fixed to a distal end of a coil sheath and thereby distal ends of the arms are displaced to approach one another to close a detect in a mucous membrane that is a target region is disclosed in Japanese Unexamined Patent Application, First Publication No. 2004-73646. In the ligation device of Japanese Unexamined Patent Application, First Publication No. 2004-73646, after distal ends of the arms are closed, coupling between the operation wire and the arms and connection between the pipe member and the coil sheath are released. As a result, the clip part is separated from the ligation device, and is placed on the tissue (the mucous membrane).

SUMMARY

A clip device according to a first aspect of an embodiment includes: a restraining tube having an insertion passage; a first arm part disposed within the insertion passage and configured to protrude from the restraining tube a second arm part disposed within the insertion passage and configured to protrude from the restraining tube, the second arm part facing the first arm part; an operation wire configured to move the first arm part in a direction from a distal end of the restraining tube to a proximal end of the restraining tube; a first stopper engaged to the first arm part; and a second stopper engaged to the second arm part, the first stopper being disposed in a region closer to the distal end of the restraining tube than the second stopper, and in response to the operation wire moving from the distal end of the restraining tube to the proximal end of the restraining tube, the first stopper is configured to (i) move relative to the second stopper, (ii) contact the second stopper, and (iii) move in contact with the second stopper. The clip device according to the first aspect ay be used in a ligation method, which includes steps of moving the first arm part relative to the second arm part by pulling in a distal end side of an operating wire connected to the first arm part such that a distal end side of the first arm part is pulled into the restraining tube; and engaging the first arm part and the second arm part by further pulling in the distal end side of the operating wire such that the distal end side of the first arm part and a distal end side of the second arm part are pulled into the restraining tube simultaneously.

As a second aspect of an embodiment, in the clip device according to the first aspect, the clip deice my further include a third stopper engaged to the second arm, the third stopper being configured to contact the first stopper and move in contact with the first stopper in response to the operation wire moving from the proximal end of the restraining tube to the distal end of the restraining tube.

As a third aspect of an embodiment, in the clip device according to the first or the second aspect, the clip device may further include a first transmitting member connecting the operating wire to the first arm part, the first stopper being provided at the first transmitting member; and a second transmitting member connected to the second arm part, the second stopper being provided at the second transmitting member.

As a fourth aspect of an embodiment, in the clip device according to the first aspect, the clip device may further include the second transmitting member is inserted through the first stopper, and the first stopper includes a hole configured to allow the first stopper and the second transmitting member to move independently from each other.

DETAILED DESCRIPTION OF THE PREFERRED EMBODIMENTS

First Embodiment

Figure 1:
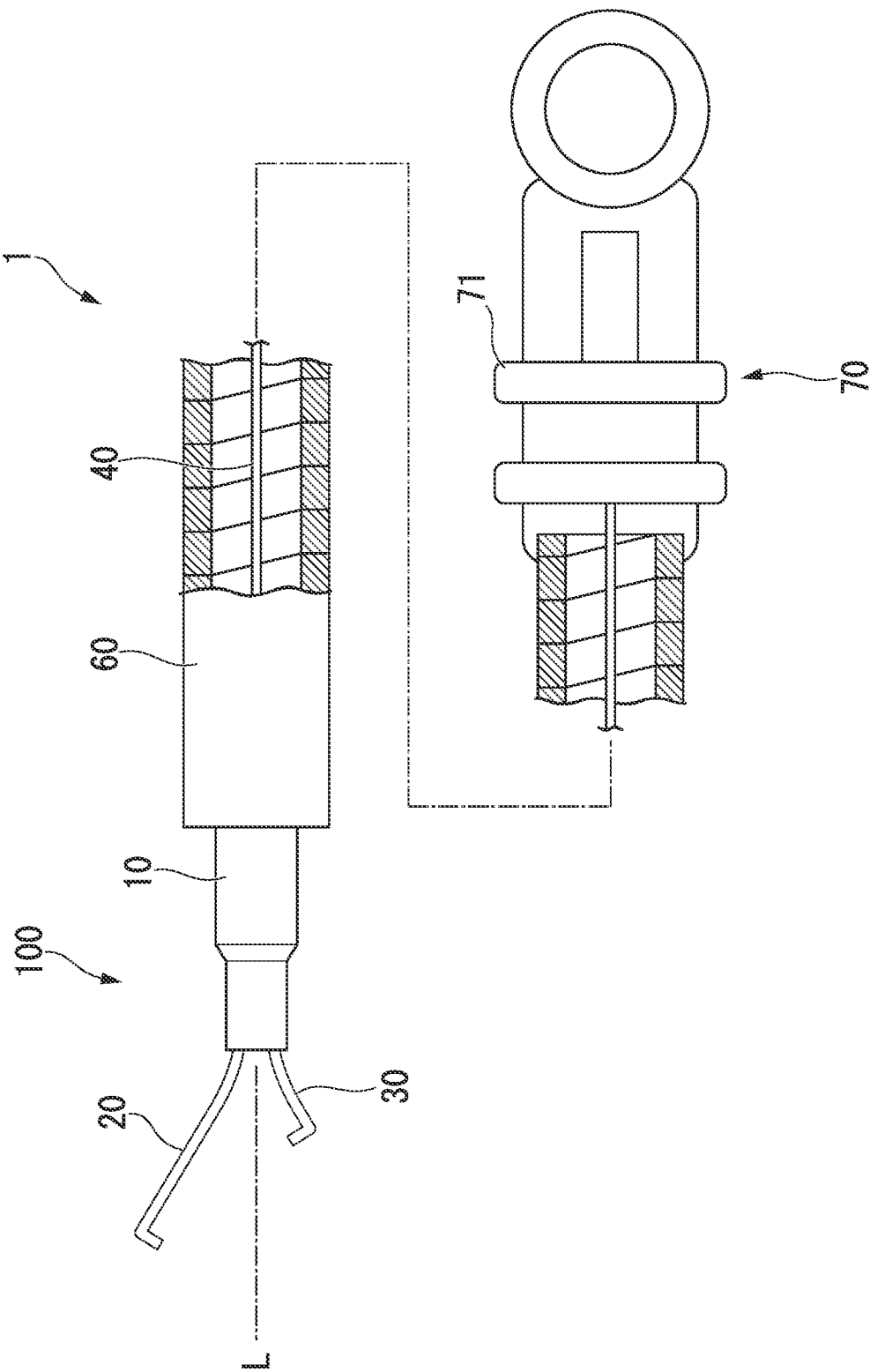
FIG. 1 is an overall view illustrating a clip device according to a first embodiment.
Figure 2:
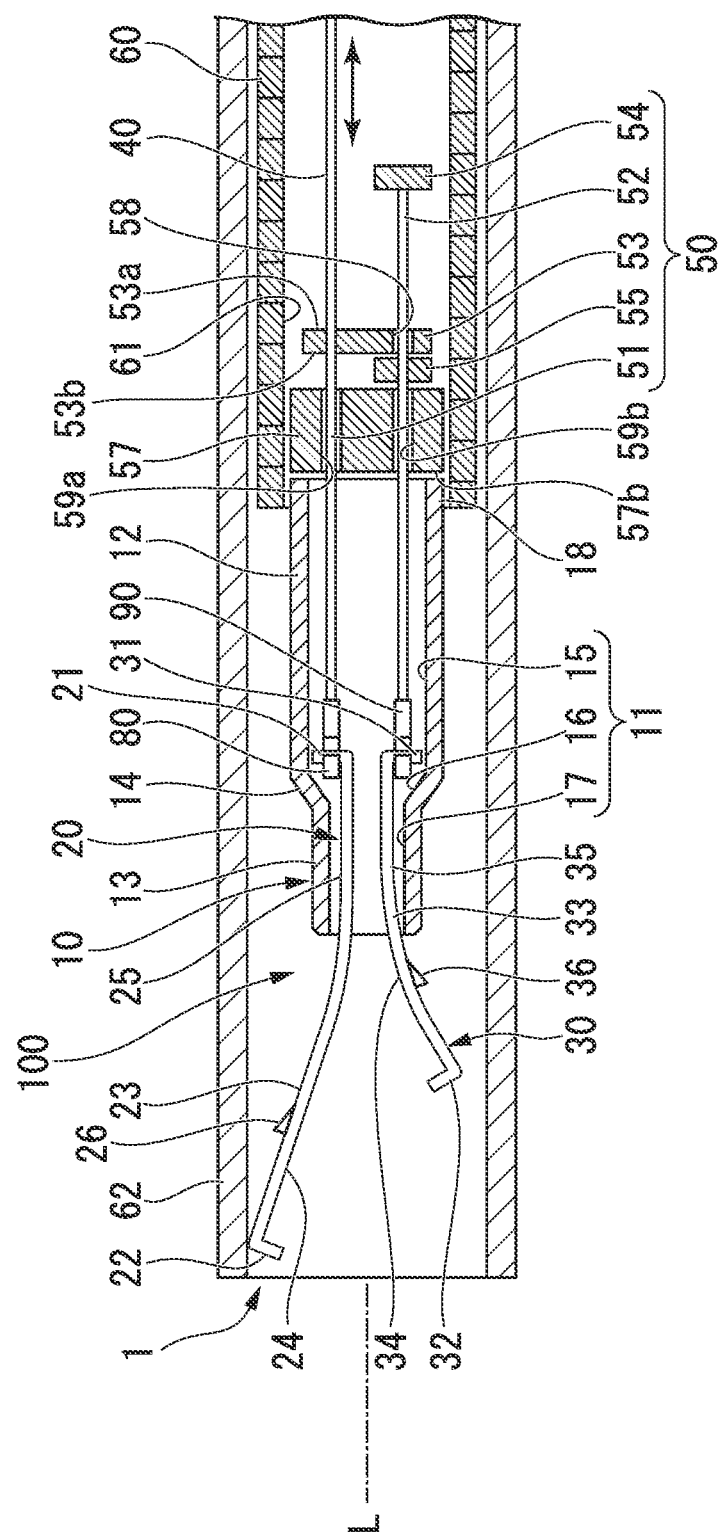
FIG. 2 is a sectional view illustrating a distal end portion of the clip device according to the first embodiment.
Figure 3:
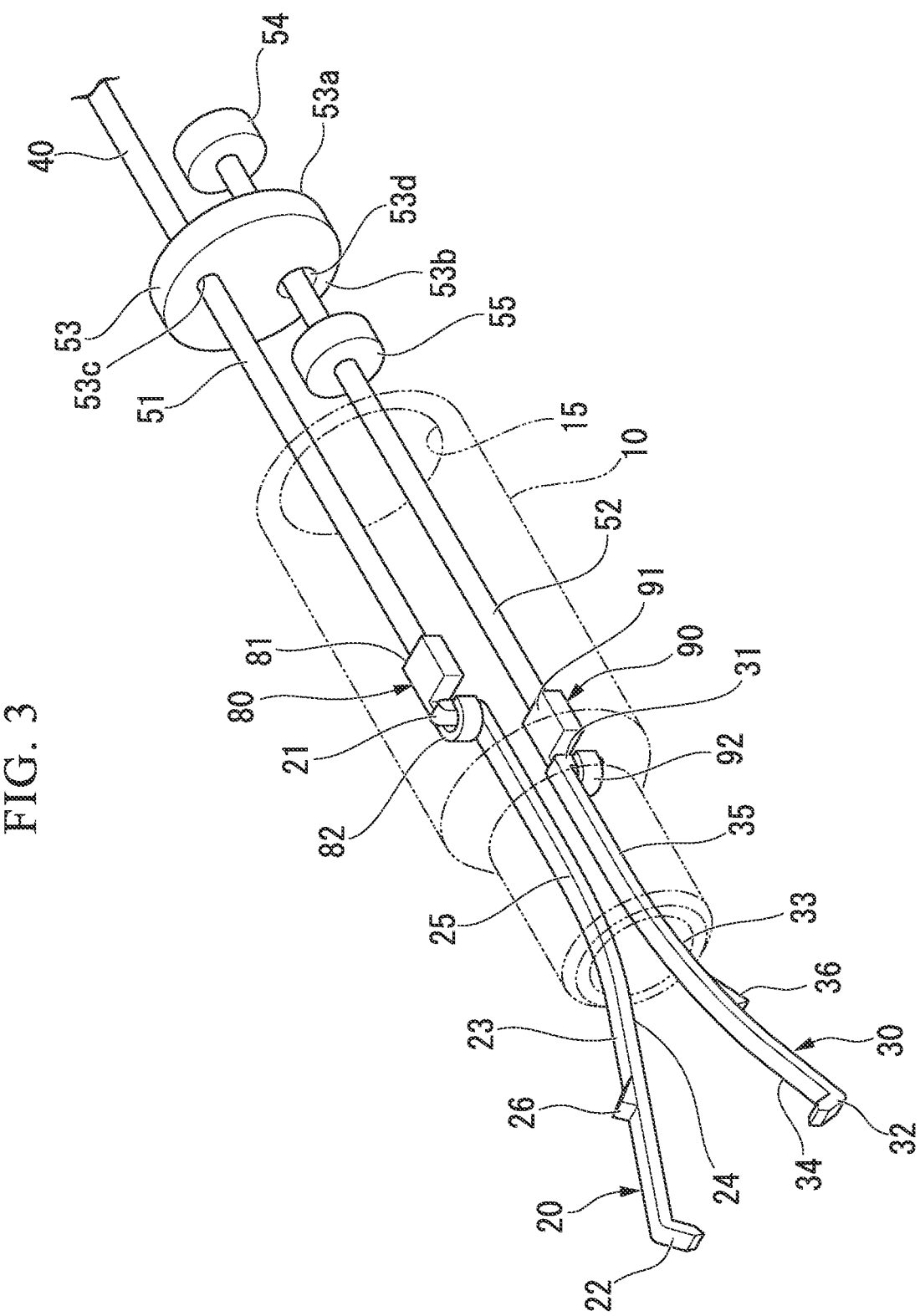
FIG. 3 is a perspective view illustrating relations among a first arm part, a second arm part, an operation wire, and a movement adjusting mechanism in the first embodiment.
Figure 4:
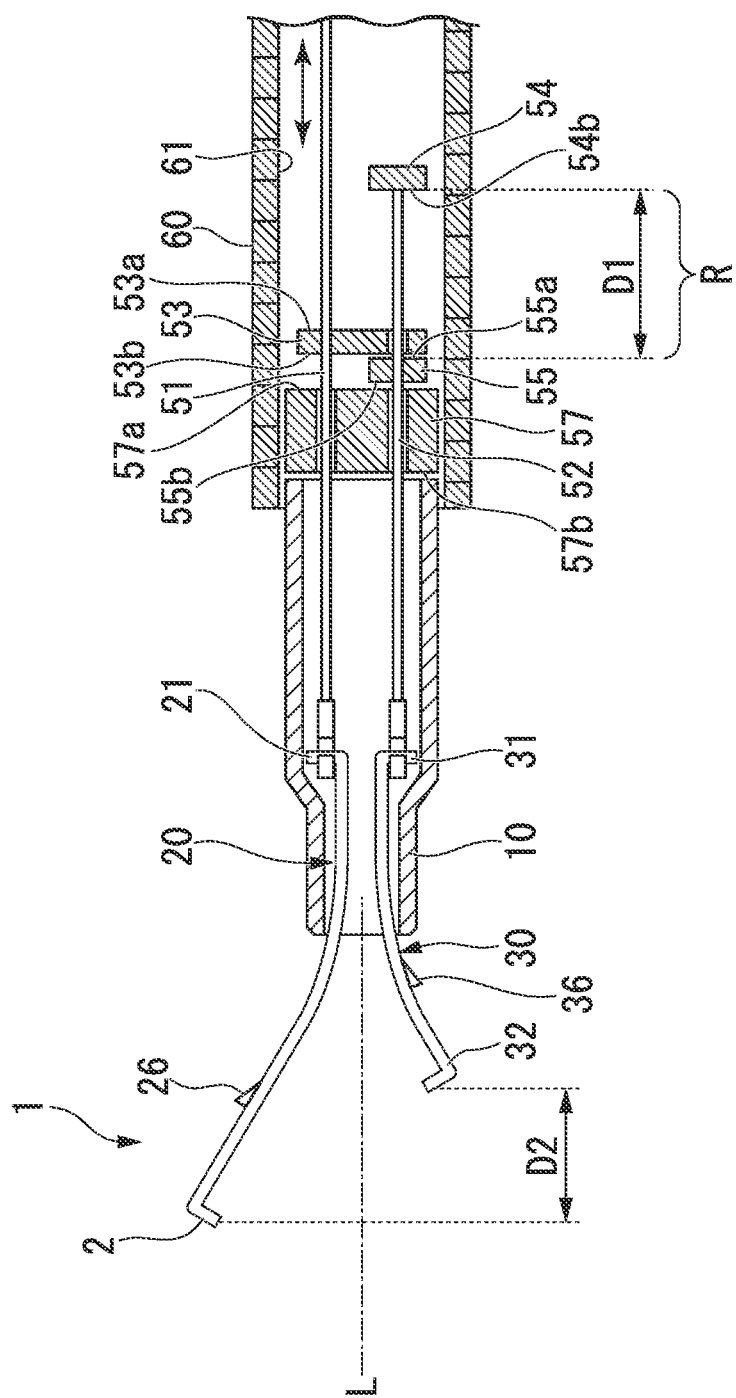
FIG. 4 is a sectional view illustrating the distal end portion of the clip device according to the first embodiment.

A clip device according to a first embodiment will be described. FIG. 1 is an overall view illustrating a clip device 1 according to the present embodiment. FIGS. 2 to 4 are sectional views illustrating a distal end portion of the clip device 1 in a plane passing through a central axis of a restraining tube 10.

As illustrated in FIGS. 1 and 2, the clip device 1 according to the present embodiment includes the restraining tube 10, a first arm part 20, a second arm part 30, an operation wire 40, and a movement adjusting mechanism 50. The clip device 1 additionally has a known sheath 60 and a known operation part 70. The clip device 1 is a device that ligates tissue in a body with a clip unit 100 which includes the restraining tube 10, the first arm part 20, and the second arm part 30 and places the clip unit 100 in the body. The restraining tube 10, the first arm part 20, the second arm part 30, the operation wire 40, and the movement adjusting mechanism 50 are provided along a longitudinal axis L of the restraining tube 10 and the sheath 60. In the following description, in the clip device 1, a side at which the first arm part 20 is provided is referred to as a distal end side, and a side which is the opposite side of the distal end side in a direction of the longitudinal axis L and at which the operation part 70 is provided is referred to as a proximal end side.

The restraining tube 10 is a tubular member having an insertion passage 11. The restraining tube 10 is inserted into a lumen 61 of a distal end of the sheath 60. The longitudinal axis L of the restraining tube 10 is located on the same axis as the central axis of the sheath 60. As illustrated in FIG. 2, the restraining tube 10 has a large diameter part 12 located at the proximal end side thereof, and a small diameter part 13 that is disposed at the distal end side thereof and is formed such that a diameter of an opening thereof is smaller than that of the large diameter part 12. The restraining tube 10 has a tapered part 14 whose diameter is reduced from a distal end of the large diameter part 12 toward a proximal end of the small diameter part 13 and which is provided between the large diameter part 12 and the small diameter part 13. The insertion passage 11 of the restraining tube 10 is formed such that an inner diameter thereof is reduced in order of a first insertion passage 15 of the large diameter part 12, a second insertion passage 16 of the tapered part 14, and a third insertion passage 17 of the small diameter part 13. The first arm part 20 and the second arm part 30 are advanceably and retreatably inserted into the insertion passage 11 in the direction of the longitudinal axis L.

The restraining tube 10 is made, for example, using either a metal material such as stainless steel, at titanium alloy (Ti-6Al-4V or the like), or a cobalt-chromium alloy or a high-rigidity resin material having proper elasticity such as polyphthalamide (PPA), polyamide (PA), or the like.

As illustrated in FIGS. 2 and 3, the first arm part 20 and the second arm part 30 are members that are inserted into the insertion passage 11 of the restraining tube 10 to protrude from a distal end of the restraining tube 10. The first arm part 20 and the second arm part 30 are formed, for example, by performing a bending process on a thin and elongate sheet made of a metal. Materials of the first arm part 20 and the second arm part 30 include, for example, stainless steel, a cobalt-chromium alloy, titanium, or the like.

The first arm part 20 has a first engaging part 21 that is disposed at the proximal end side, and a first claw part 22 and a first curved part 23 that are provided at the distal end side. In the present embodiment, the first arm part 20 performs a bending process on one plate made of stainless steel, and thereby the first engaging part 21, the first curved part 23, and the first claw part 22 are formed. In the following description, in the first arm part 20, a surface that faces the second arm part 30 when inserted into the restraining tube 10 is referred to as an inner surface 24, and a surface that is a surface of the opposite side of the inner surface 24 and faces the insertion passage 11 of the restraining tube 10 is referred to as an outer surface 25. The first engaging part 21 is formed by performing a bending process such that a proximal end part of the first arm part 20 is bent from the inner surface 24 toward the outer surface 25 in an approximate J shape. The first engaging part 21 is connected to a first coupling member (to be described below).

The first claw part 22 is formed in a hook shape by performing a bending process such that a distal end of the first arm part 20 is bent toward the inner surface 24. A distal end of the first claw part 22 may be formed in a sawtooth shape.

The first curved part 23 is curved like a bow away from and inclined with respect to the longitudinal axis L of the restraining tube 10 and is formed between the first engaging part 21 and the first claw part 22. The first curved part 23 is subjected to a bending process into the above-mentioned shape in advance, and is formed to be elastically deformed when an external force acts thereon and to be restored to the curved shape in a natural state in which no external force acts thereon.

As illustrated in FIGS. 2 and 3, a first protrusion part 26 is provided on the outer surface 25 of the distal end side of the first arm part 20. The first protrusion part 26 protrudes from the outer surface 25 in a thickness direction of the first arm part 20 in a sawtooth shape. To be specific, the first protrusion part 26 has a right-triangle shape in the side view, extends from the outer surface 25 of the distal end side of the first arm part 20 at a distal end side thereof in a vertical direction, has an acute angle part formed at an outer end thereof, and has a shape that is inclined with respect to the outer surface 25 at a proximal end side thereof than the angle part.

The first engaging part 21 of the first arm part 20 is disposed in the first insertion passage 15 of the restraining tube 10 and threaded through the second insertion passage 16 and the third insertion passage 17, and a region of the distal end side of the first arm part 20 including the first claw part 22 is disposed to protrude from the distal end of the restraining tube 10.

As illustrated in FIGS. 2 and 3, the second arm part 30 is generally formed similar to the first arm part 20, and is inserted into the insertion passage 11 to protrude from the distal end of the restraining tube 10. The second arm part 30 has a second engaging part 31 and a second claw part 32. In the following description, of the second arm part 30, a surface that faces the first arm part 20 when inserted into the restraining tube 10 is referred to as an inner surface 34, and a surface that is a surface of the opposite side of the inner surface 34 and faces the insertion passage 11 of the restraining tube 10 is referred to as an outer surface 35. The second engaging part 31 is formed by performing a bending process such that a proximal end of the second arm part 30 is bent from the inner surface 34 toward the outer surface 35 in an approximate J shape. The second engaging part 31 is connected to a second coupling member (to be described below).

The second arm part 30 has the second claw part 32, a second curved part 33, and a second protrusion part 36, like the first claw part 22, the first curved part 23, and the first protrusion part 26 of the first arm part 20.

The second engaging part 31 of the second arm part 30 is disposed in the first insertion passage 15 of the restraining tube 10 and threaded through the second insertion passage 16 and the third insertion passage 17, and a region of the distal end side of the second arm part 30 including the second claw part 32 is disposed to protrude from the distal end of the restraining tube 10.

A size of the second arm part 30 in a longitudinal direction is shorter than that of the first arm part 20 in a longitudinal direction. The first arm part 20 and the second arm part 30 are disposed to be curved away from each other in a state in which the curved parts 23 and 33 thereof protrude from the distal end of the restraining tube 10. In this case, the distal end (the first claw part 22) of the first arm part 20 in the direction of longitude axis L is located at the distal end side than the distal end (the second claw part 32) of the second arm part 30.

The inner surfaces 24 and 34 of the first and second engaging parts 21 and 31 are disposed face to each other in the first insertion passage 15 of the restraining tube 10 along the longitudinal axis L of the restraining tube 10, and ends of the first and second engaging parts 21 and 31 extend away from the longitudinal axis L. A distance between the end of the first engaging part 21 and the end of the second engaging part 31 is longer than a diameter of an opening of the third insertion passage 17 of the restraining tube 10. For this reason, the first engaging part 21 and the second engaging part 31 are subjected to the regulation of movement thereof to the distal end side from the second insertion passage 16 of the restraining tube 10.

The sheath 60 is a coil sheath in which element wires are tightly wound in the direction of the longitudinal axis L. The sheath 60 has flexibility and a structure resistant to the compressive force in the direction of the longitudinal axis L. As illustrated in FIG. 1, the operation part 70 is connected to a proximal end of the sheath 60. The well-known operation wire 40 is inserted into the sheath 60, and a proximal end of the operation wire 40 is connected to a slider 71 of the operation part 70. A distal end side of the operation wire 40 is connected to the first arm part 20. Due to an operation of an operator sliding the slider 71 of the operation part 70, the operation wire 40 is advanced and retreated in the sheath 60, and advances and retreats the first arm part 20 in the restraining tube 10.

The movement adjusting mechanism 50 is a mechanism in which a state in which the first arm part 20 advances and retreats independently of the second arm part 30 and a state in which the second arm part 30 retreats along with the retreat of the first arm part 20 when the operation wire 40 is operated for retreat by a predetermined amount are selectively realized. The movement adjusting mechanism 50 is provided with a first transmitting member 51, a second transmitting member 52, a first stopper 53, and a second stopper 54.

The first transmitting member 51 is a linear member, and is connected to the distal end of the operation wire 40. As illustrated in FIGS. 2 and 3, the first stopper 53 is provided for a connecting part between the first transmitting member 51 and the operation wire 40. The first stopper 53 is an approximate disc-like member that has a diameter smaller than an inner diameter of the lumen 61 of the sheath 60. A first through-hole 53c is formed in the first stopper 53, and the distal end of the operation wire 40 and a proximal end of the first transmitting member 51 are inserted into and fixed to the first through-hole 53c.

A first coupling member 80 is connected to a distal end of the first transmitting member 51. The first coupling member 80 is formed of a metal or resin material. The first coupling member 80 is formed of a flat plate that is long in an axial direction of the operation wire 40, and has a first coupling part 81 and a first hook part 82. The first coupling part 81 is connected to the distal end of the first transmitting member 51. The first hook part 82 engages the first engaging part 21 of the first arm part 20. That is, the operation wire 40 and the first arm part 20 are connected via the first transmitting member 51 and the first coupling member 80. The first coupling member 80 and the first engaging part 21 are disposed in the first insertion passage 15 of the large diameter part 12 of the restraining tube 10, and are detachably connected.

The second transmitting member 52 is a linear member, is connected to the second arm part 30, and is provided to advance and retreat the second arm part 30. A second coupling member 90 is connected to a distal end of the second transmitting member 52. Like the first coupling member 80, the second coupling member 90 is formed of a metal or resin material. The second coupling member 90 is formed of a flat plate that is long in an axial direction of the operation wire 40, and has a second coupling part 91 and a second hook part 92. The second coupling part 91 is connected to the distal end of the second transmitting member 52. The second hook part 92 engages the second engaging part 31 of the second arm part 30. The second coupling member 90 and the second engaging part 31 are disposed in the first insertion passage 15 of the large diameter part 12 of the restraining tube 10, and are detachably connected.

The second transmitting member 52 is disposed to extend approximately parallel to the first transmitting member 51. A second through-hole 53d, which extends parallel to the first through-hole 53c and passes through the first stopper 53, is formed in the first stopper 53. The second through-hole 53d has a diameter greater than an outer diameter of the second transmitting member 52, and the second transmitting member 52 is retreatably inserted into the second through-hole 53d.

The second stopper 54 is provided at a proximal end of the second transmitting member 52. The second stopper 54 is a columnar member having a diameter greater than the outer diameter of the second transmitting member 52, and has a distal end face 54b that is substantially parallel to a proximal end face 53a of the first stopper 53. A length of the second transmitting member 52 is longer than that of the first transmitting member 51.

The movement adjusting mechanism 50 further has a third stopper 55 and a ring member 57. The third stopper 55 is fixed to an outer circumference of the second transmitting member 52 at the distal end side than the first stopper 53 and the second stopper 54. The third stopper 55 is an annular member having an outer diameter greater than an opening width of the second through-hole 53d, and has a proximal end face 55a that is substantially parallel to the distal end face 53b of the first stopper 53.

The ring member 57 is an approximately columnar member, and is fixed in the lumen 61 of the distal end of the sheath 60. To be specific, an outer circumferential surface of the ring member 57 and the lumen 61 of the distal end of the sheath 60 are fixed by well-known fixing means such as an adhesive. Two lumens (a first lumen 59a and a second lumen 59b) that penetrate to extend in an axial direction are formed in the ring member 57. The first transmitting member 51 is inserted to be advanceable and retreatable in the first lumen 59a of the ring member 57, and the second transmitting member 52 is inserted to be advanceable and retreatable in the inside of the second lumen 59b. Therefore, the first transmitting member 51 and the second transmitting member 52 are configured to be advanceable and retreatable in the ring member 57 while maintaining a state in which they extend in parallel. A proximal end 18 of the restraining tube 10 inserted into the lumen 61 of the sheath 60, and the proximal end 18 of restraining tube 10 is disposed in contact with the distal end face 57b of the ring member 57.

Since the first transmitting member 51 and the operation wire 40 are fixed to the first stopper 53, the first stopper 53 advances and retreats in the sheath 60 depending on the advance and retreat of the operation wire 40 due to an operation of the operation part 70. As illustrated in FIG. 2, the first stopper 53 is provided between the second stopper 54 fixed to the proximal end of the second transmitting member 52 and the third stopper 55 fixed to a middle portion (the distal end side than the second stopper 54) of the second transmitting member 52 to be advanceable and retreatable in association with the advance and retreat of the first transmitting member 51.

Positional relations among the first stopper 53, the second stopper 54, and the third stopper 55 in the direction of the longitudinal axis L are set such that the movement adjusting mechanism 50 can switch advance and retreat positions of the first arm part 20 and the second arm part 30 in relation to the restraining tube 10 and opened and closed states of the first arm part 20 and the second arm part 30. The movement adjusting mechanism 50 is configured such that a range (a first range) in which the first arm part 20 moves independently of the second arm part 30 and a range (a second range) in which the second arm part 30 moves along with an advance and retreat motion of the first arm part 20 can be switched depending on a position of the operation wire 40 in relation to the restraining tube 10. The details will be described below.

Next, a connecting structure of each member of the clip device 1 and an operation of the movement adjusting mechanism 50 will be described.

As illustrated in FIGS. 1 and 2, the ring member 57 is fixed to the lumen 61 of the sheath 60 at the proximal end side that is slightly than an opening of the distal end of the sheath 60. The restraining tube 10 is inserted into the opening of the distal end of the sheath 60, and the proximal end 18 of restraining tube 10 is in contact with the distal end face 57b of the ring member 57.

The operation part 70 is connected to the proximal end of the sheath 60, and the operation wire 40 connected to the slider 71 of the operation part 70 is inserted into the lumen 61 and extends to the distal end of the sheath 60. In the inside of the sheath 60, the distal end of the operation wire 40 is inserted into the first through-hole 53c of the first stopper 53 and is fixed to the first stopper 53 along with the proximal end of the first transmitting member 51. The first transmitting member 51 is inserted into one lumen (the first lumen 59a) of the ring member 57, and is disposed in the large diameter part 12. As illustrated in FIG. 3, the distal end part of the first transmitting member 51 is fixed to a proximal end of the first coupling member 81 of the first coupling member 80. The first hook part 82 of the first coupling member 80 is engaged with the first engaging part 21 of the first arm part 20.

The second transmitting member 52, to the proximal end of which the second stopper 54 is fixed, is inserted into the second through-hole 53d of the first stopper 53 and one lumen (the second lumen 59b) of the ring member 57, and the distal end thereof is fixed to a proximal end of the second coupling part 91 of the second coupling member 90. The second hook part of the second coupling member 90 and the second engaging part 31 of the second arm part 30 are engaged. The second arm part 30, the second coupling member 90, and the second transmitting member 52 are retreatably supported in the restraining tube 10 by the restraining tube 10, the second lumen 59b of the ring member 57, and the second through-hole 53d of the first stopper 53.

The restraining tube 10, the first arm part 20, and the second arm part 30 are provided to be mountable and demountable on the sheath 60. The first arm part 20 is engaged on the first coupling member 80, and the second arm part 30 is engaged on the second coupling member 90. Thereby, abutting of the restraining tube 10 with the ring member 57 is maintained.

Since the operation wire 40 and the first arm part 20 have the connecting structure, the advance and retreat motion of the operation wire 40 is directly transmitted to the first arm part 20, and the first arm part 20 is advanced and retreated. A relation between the advance and retreat motion of the operation wire 40 and the advance and retreat of the first arm part 20 is maintained in a state in which the first arm part 20 is engaged on the first coupling member 80. The second transmitting member 52 is provided to be advanceable and retreatable in the second through-hole 53d of the first stopper 53. Therefore, as illustrated in FIG. 4, when the first stopper 53 is located between the second stopper 54 and the third stopper 55 (the first range R) in the direction of the longitudinal axis L, the first stopper 53 moves relative to the second transmitting member 52. As the second transmitting member 52 is advanced and retreated in the sheath 60, the second arm part 30 is advanced and retreated, and hence the operation wire 40 and the first transmitting member 51 are advanced and retreated independently of the second transmitting member 52. Therefore, while the first stopper 53 is located in the first range, the first arm part 20 is advanced and retreated independently of the second arm part 30.

Figure 5:
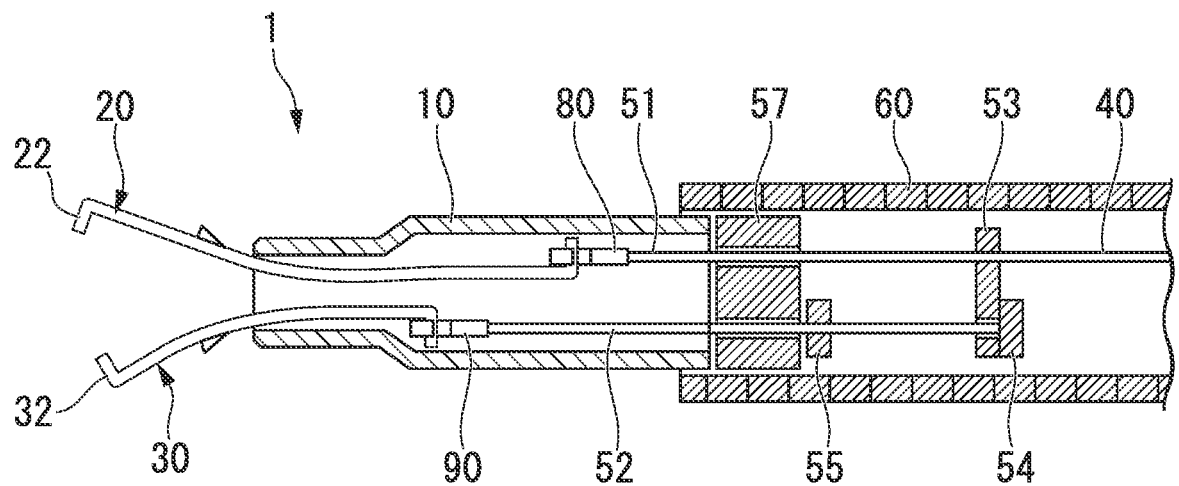
FIG. 5 is a sectional view illustrating the distal end portion of the clip device according to the first embodiment.
Figure 6:
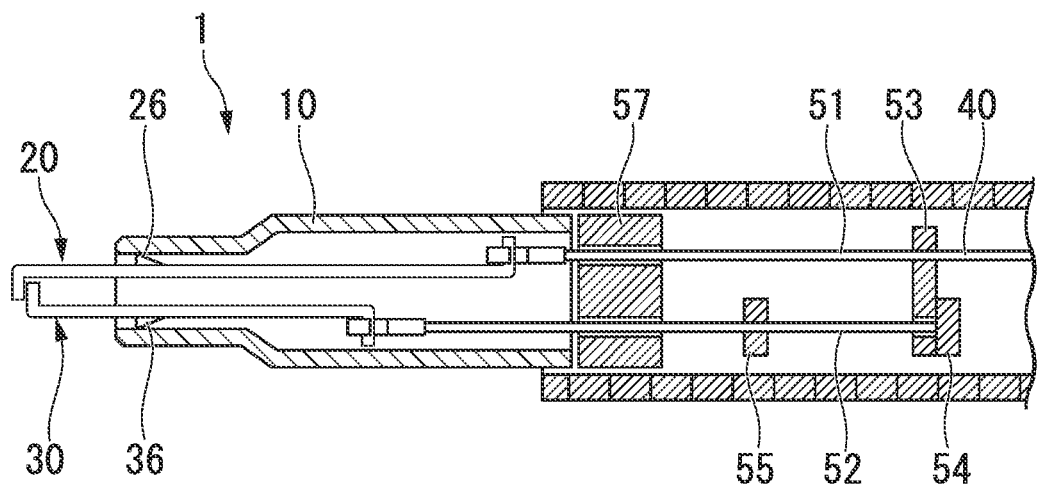
FIG. 6 is a sectional view illustrating the distal end portion of the clip device according to the first embodiment.

As illustrated in FIGS. 5 and 6, when the first stopper 53 is advanced and retreated at a position (in the second range) at which it is in contact with the second stopper 54 or the third stopper 55, the second stopper 54 or the third stopper 55 is pressed against the first stopper 53 so that the second transmitting member 52 is advanced and retreated along with the advance and retreat of the first transmitting member 51. That is, as illustrated in FIG. 5, when the operation wire 40 is further pushed in a state in which the distal end face 53b of the first stopper 53 is in contact with the proximal end face 55a of the third stopper 55, the third stopper 55 is pressed against the distal end side by the first stopper 53 so that the second transmitting member 52 is also advanced to the distal end side. As a result, the second arm part 30 is advanced to the distal end side in the restraining tube 10. As illustrated in FIG. 6, when the operation wire 40 is further pulled in a state in which the proximal end face 53a of the first stopper 53 is in contact with the distal end face 54b of the second stopper 54, the second stopper 54 is pressed against the proximal end side by the first stopper 53 so that the second transmitting member 52 also retreats to the proximal end side. As a result, the second arm part 30 moves to the proximal end side in the restraining tube 10.

Therefore, when a fixed position of the first stopper 53 to the first transmitting member 51 and fixed positions of the second stopper 54 and the third stopper 55 to the second transmitting member 52 are set on the basis of amounts of protrusion of the first and second arm parts 20 and 30 from the restraining tube 10, for example, as illustrated in FIG. 4, a separation distance D1 between the distal end face 54b of the second stopper 54 and the proximal end face 55a of the third stopper 55 is set to be nearly equal to a distance D2 between the first claw part 22 and the second claw part 32 in the direction of the longitudinal axis L when the first arm part 20 and the second arm part 30 fully protrude from the restraining tube 10. The fixed position of the third stopper 55 to the second transmitting member 52 is set depending on a position at which only the first arm part 20 moves to the proximal end side of the restraining tube 10 and a length of protrusion of the second arm part 30 from the restraining tube 10 becomes the maximum.

The clip device 1 is assembled according to the following procedure.

The first arm part 20 and the second arm part 30 are inserted into the restraining tube 10, and the inner surfaces 24 and 34 of the first and second arm parts 20 and 30 are disposed in the first insertion passage 15 to face each other.

In a state in which the second coupling member 52 is provided for the operation wire 40 and the first transmitting member 51 via the first stopper 53, the first coupling member 80 and the second coupling member 90 are inserted into the respective lumens 59a and 59b of the ring member 57, and are projected from the distal end of the sheath 60. The first coupling member 80 and the second coupling member 90 are respectively engaged on the first engaging part 21 and the second engaging part 31 inside the restraining tube 10. In this state, the proximal end part of the restraining tube 10 is inserted into the lumen 61 from the opening of the distal end of the sheath 60, and is brought into contact with the distal end face 57b of the ring member 57. When the slider 71 is pulled to the proximal end side, the restraining tube 10, the first arm part 20, and the second arm part 30 are coupled to the sheath 60.

In this state, the clip device 1 becomes in an initial state that can be used for a procedure. As illustrated in FIG. 2, when the clip device 1 in the initial state is inserted into an outer sheath 62 and the first arm part 20 and the second arm part 30 are accommodated in the outer sheath 62, the first arm part 20 is elastically deformed toward the longitudinal axis L. The outer sheath 62 into which the clip device 1 is inserted is inserted into an endoscope insertion part of an endoscopic device (not shown), and the clip device 1 is used for a ligation procedure.

Next, an operation of the clip device 1 when a ligation procedure is performed will be described using FIGS. 1 to 9 with an example in which a mucous membrane T inside a digestive tract is ligated.

First, the endoscope insertion part of the endoscopic device is inserted to the vicinity of a target region inside the digestive tract. Subsequently, an operator ejects the clip device 1 in the state illustrated in FIG. 2 to protrude from a distal end of the endoscope insertion part and the distal end of the outer sheath 62.

The operator slides the slider 71 to the distal end side with the first arm part 20 full projected from the restraining tube 10. That is, when the slider 71 of the operation part 70 is slid to the distal end side, the operation wire 40 moves to the distal end side relative to the sheath 60, and the first coupling member 80 is ejected to the distal end side. When the first coupling member 80 is ejected to the distal end side, the first engaging part 21 is pressed against the distal end side by a proximal end part of a cutout of the first hook part 82, and the first arm part 20 is disposed at a position at which it fully protrudes from the distal end of the restraining tube 10.

When the first arm part 20 moves to the position at which it fully protrudes from the distal end of the restraining tube 10, the distal end face 35b of the first stopper 53 comes into contact with the proximal end face 55a of the third stopper 55. For this reason, the third stopper 55 is pressed along with the advance of the first transmitting member 51 so that the second transmitting member 52 is advanced, and the second arm part 30 is disposed at a position at which it fully protrudes from the distal end of the restraining tube 10. As the third stopper 55 is provided, the second arm part 30 can be finely adjusted in use stage when shifted to the proximal end side than a given position.

When the first arm part 20 and the second arm part 30 are disposed at the positions at which they fully protrude from the distal end of the restraining tube 10, the first arm part 20 and the second arm part 30 are subjected to release of a pressing force by the restraining tube 10 and restoration of the curved shape, and the first claw part 22 and the second claw part 32 move away from the longitudinal axis L. Further, since the first arm part 20 is longer than the second arm part 30 and protrudes from the restraining tube 10, the position of the distal end (the first claw part 22) of the first arm part 20 in the direction of the longitudinal axis L is located at the distal end side than the distal end (the second claw part 32) of the second arm part 30.

Figure 7:
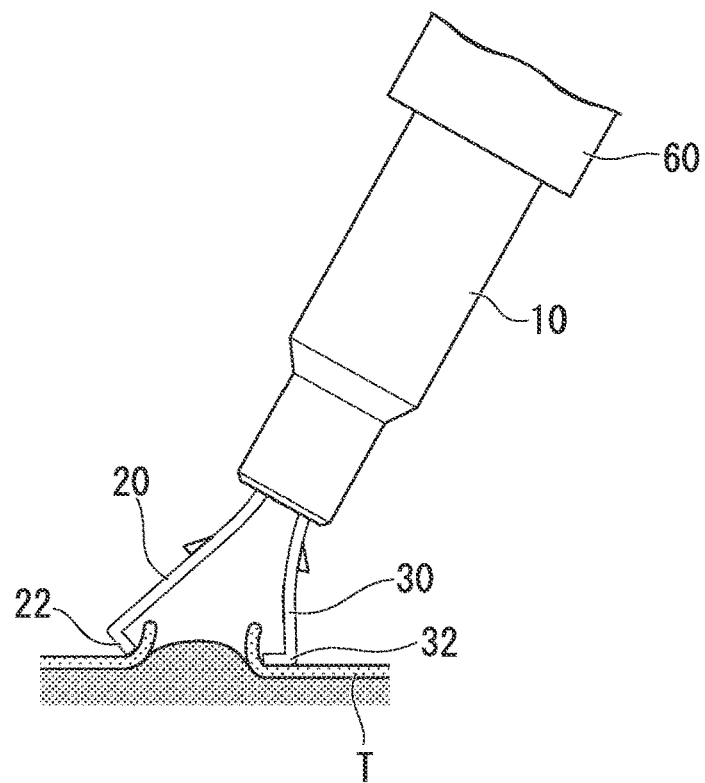
FIG. 7 is a view illustrating a usage aspect of the clip device according to the first embodiment.

Next, the operator presses the second claw part 32 against the mucous membrane T in the vicinity of a ligation region. Then, the endoscope insertion part is advanced inside the digestive tract. Since the ligation region is the mucous membrane T of the digestive tract, the clip device 1 approaches the mucous membrane T in a direction inclined with respect to the mucous membrane T. Then, since the first claw part 22 is spaced and located at the distal end side than the second claw part 32, when the second claw part 32 is pressed against the mucous membrane T in the inclined direction, the first claw part 22 comes into contact with the mucous membrane T as illustrated in FIG. 7.

Figure 8:
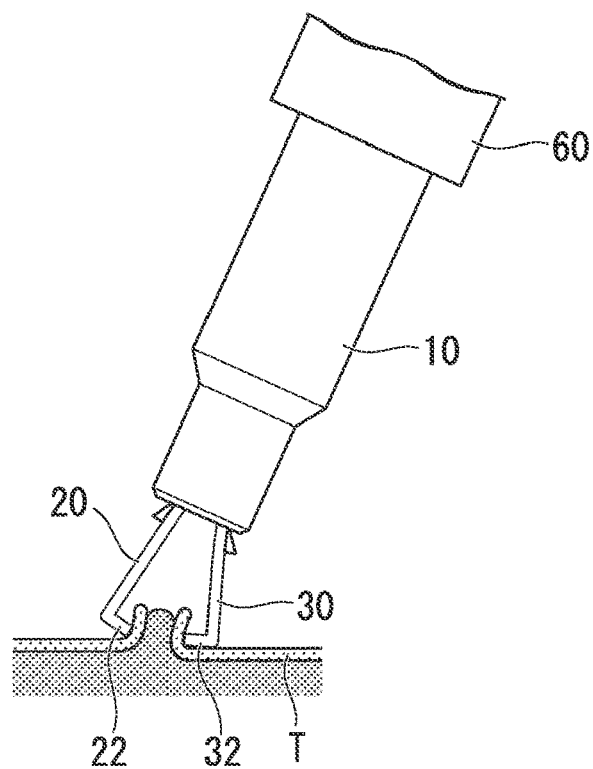
FIG. 8 is a view illustrating the usage aspect of the clip device according to the first embodiment.
Figure 9:
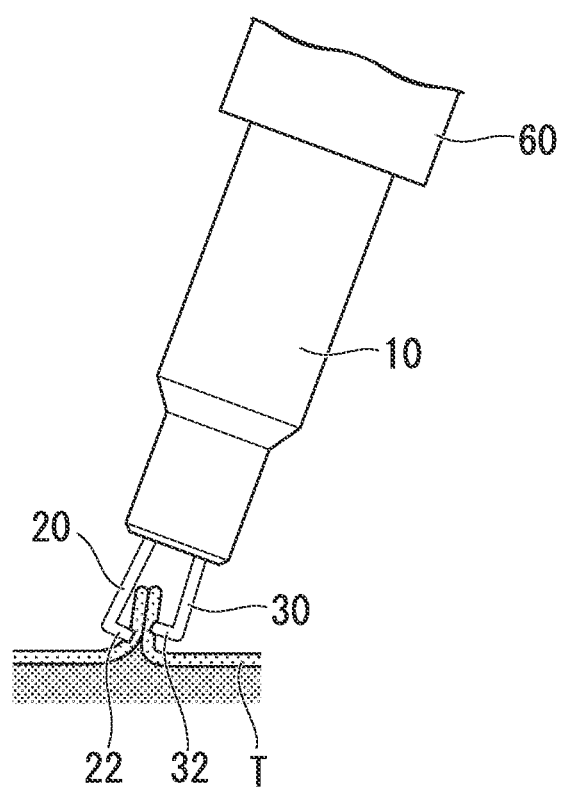
FIG. 9 is a view illustrating the usage aspect of the clip device according to the first embodiment.

Subsequently, the operator pushes the clip device 1 to the distal end side, and pulls the slider 71 of the operation part 70 to the proximal end side with the first claw part 22 and the second claw part 32 pressed against the mucous membrane T. When the slider 71 is pulled to the proximal end side, the first arm part 20 moves (retreats) to the proximal end side in the restraining tube 10 due to the operation wire 40. As the first arm part 20 is pulled into the restraining tube 10, the outer surface 25 is pressed by the inner surface of the third insertion passage 17 so that a curvature of the first curved part 23 is reduced. Then, the first claw part 22 moves along a locus of the direction inclined with respect to the proximal end side to approach the second claw part 32, and approaches the second claw part 32 to enter a leg closed state (FIG. 8). As a result, the first arm part 20 and the second arm part 30 function as a grasping part of the mucous membrane T. Then, the proximal end face 53a of the first stopper 53 comes into contact with the distal end face 54b of the second stopper 54.

When the operator further pulls the slider 71 to the proximal end side, the first stopper 53 moves to the proximal end side while in contact with the second stopper 54. As a result, the second stopper 54 is pressed so that the second transmitting member 52 retreats along with the first transmitting member 51. As a result, the first arm part 20 and the second arm part 30 are simultaneously pulled to the proximal end side of the restraining tube 10 with the mucous membrane T grasped between the first claw part 22 and the second claw part 32. As illustrated in FIG. 6, when the first arm part 20 and the second arm part 30 are fully pulled to the proximal end side, the first claw part 22 and the second claw part 32 are disposed to overlap each other in a diameter direction of the restraining tube 10. For this reason, the mucous membrane T between the first claw part 22 and the second claw part 32 is more strongly pinched.

After the first arm part 20 and the second arm part 30 are pulled into the restraining tube 10 by a predetermined amount, the first protrusion part 26 provided for the outer surface 25 of the first arm part 20 and the second protrusion part 36 provided for the outer surface 35 of the second arm part 30 are pushed into the third insertion passage 17. Since the first protrusion part 26 and the second protrusion part 36 have the sawtooth shape mentioned above, the first and second protrusion parts 26 and 36 are brought into contact with an inner wall of the third insertion passage 17 under pressure, and the first arm part 20 and the second arm part 30 can move in a direction in which they are pulled to the proximal end side (in a leg closing direction of the first arm part 20), but movement in a direction in which they are ejected to the distal end side (in a direction in which the first arm part 20 protrudes from the restraining tube 10 and undergoes leg opening) is regulated by the first and second protrusion parts 26 and 36 acting as a wedge that cuts into the inner wall of the third insertion passage 17. Thereby, a force for pulling the slider 71 to the proximal end side is increased, and an operator can recognize that the first arm part 20 and the second arm part 30 are accommodated in the restraining tube 10 up to a given position.

Subsequently, when the operation wire 40 is further pulled in a state in which the mucous membrane T is held by the first arm part 20 and the second arm part 30, the first arm part 20 and the second arm part 30 do not move because the movement to the proximal end side is regulated. For this reason, a great load is applied to the first hook part 82 and the second hook part 92 so that the first and second hook parts 82 and 92 are subjected to plastic deformation, and the engaging of the first engaging part 21 and the first hook part 82 is released. As a result, the connection between the first transmitting member 51 and the first arm part 20 and the connection between the second transmitting member 52 and the second arm part 30 are released.

Figure 10:
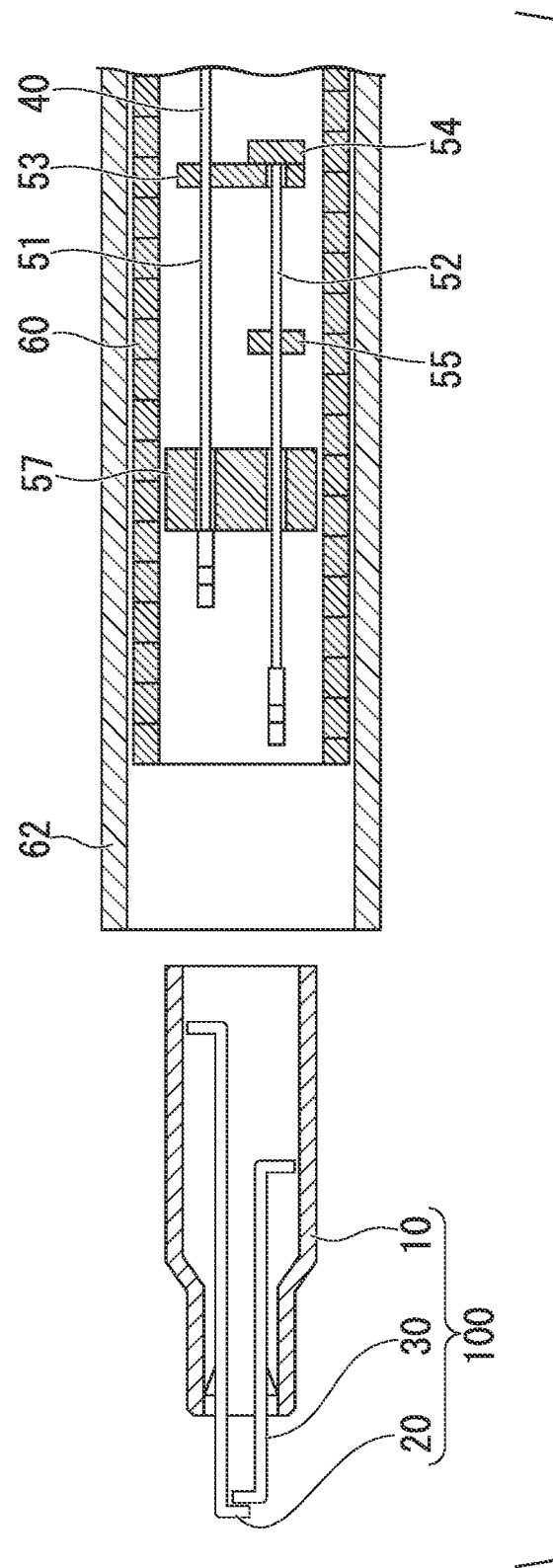
FIG. 10 is a sectional view illustrating the distal end portion of the clip device according to the first embodiment.

When the connection between the operation wire 40 and the first arm part 20 is released as described above, abutting of the proximal end of the restraining tube 10 with the distal end of the ring member 57 is also released. As illustrated in FIG. 10, the restraining tube 10 falls from the sheath 60, and the clip unit 100 is placed by ligating the mucous membrane T. Afterwards, the sheath 60, the operation wire 40, and the coupling member 90 are pulled out from the endoscope insertion part, and the clip device 1 is removed.

According to the clip device 1 according to the present embodiment, the position of the first claw part 22 in the direction of the longitudinal axis L of the restraining tube 10 in the initial state is located at the distal end side than the position of the second claw part 32. For this reason, in the clip device 1, when the clip unit 100 is brought close to the ligation region in the inclined direction and performs the ligation, the first claw part 22 and the second claw part 32 can both enter a state in which they come into contact with tissue. Therefore, when the mucous membrane or the like of the digestive tract is ligated through an endoscope, a process in which the mucous membrane T is pinched and ligated by the first arm part 20 and the second arm part 30 can be smoothly performed.

Since the second arm part 30 does not follow the motion (the retreat motion) in which the first arm part 20 is pulled until the first claw part 22 approaches the second claw part 32, the position of the second arm part 30 with respect to the tissue can be fixed. Therefore, in comparison with a conventional clip unit, the operation of pulling the clip unit to the proximal end side is facilitated while the tissue is pressed.

The mode of the present embodiment is not limited to the foregoing. For example, the first stopper and the second stopper can smoothly perform the ligation of the tissue as in the embodiment even when the following modifications are considered and appropriately combined.

Modifications of First and Second Stoppers

Figure 11:
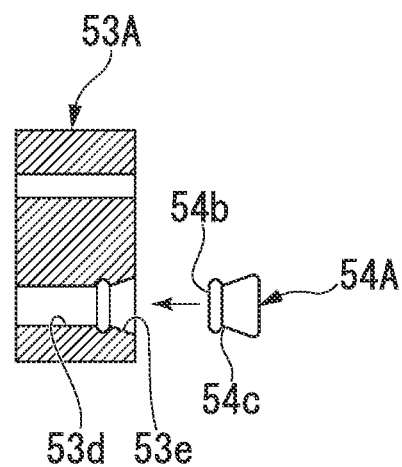
FIG. 11 is a sectional view illustrating first modifications of a first stopper and a second stopper in the first embodiment.
Figure 12:
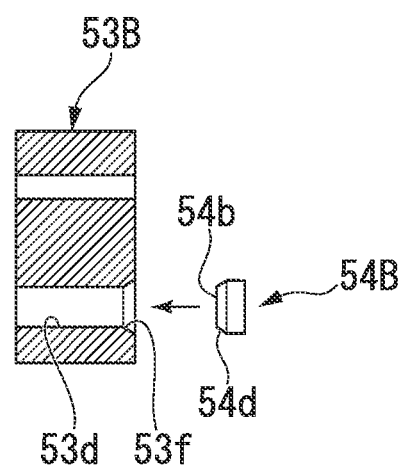
FIG. 12 is a sectional view illustrating second modifications of the first stopper and the second stopper in the first embodiment.

FIGS. 11 and 12 are sectional views illustrating modifications of the first and second stoppers. The first and second stoppers in the present embodiment may be configured as in the modifications illustrated in FIGS. 11 and 12. That is, the second stopper may be configured to be fitted into the second through-hole of the first stopper when the first stopper is pressed against the second stopper with a strong force. For example, in a first modification illustrated in FIG. 11, a recess 54c in which an outer circumference of the second stopper 54A is reduced in diameter in a circumferential direction is formed at a side closer to a distal end face 54b than a middle portion of the second stopper 54A in the direction of the longitudinal axis L. An opening 53e of the proximal end side of the second through-hole 53d of the first stopper 53A is formed in an uneven shape corresponding to a shape of the distal end side of the second stopper 54A.

In a second modification illustrated in FIG. 12, an outer periphery of the distal end face 54b of the second stopper 54B is chamfered, and a tapered face 54d corresponding to a shape of the distal end side of the second stopper 54A is formed in an opening 53f of the proximal end side of the second through-hole 53d of the first stopper 53A. The first stoppers 53A and 53B and the second stoppers 54A and 54B in the first and second modifications are formed to allow them to be inserted into the openings 53e and 53f of the proximal end sides of the second through-holes 53d under pressure.

After the first arm part 20 and the second arm part 30 enter a closed state, when the operation wire 40 is further pulled to the proximal end side, a great force is applied between the first stopper and the second stopper. In the case of the first stoppers 53A and 53B and the second stoppers 54A and 54B of the above modifications, the distal end sides of the second stoppers 54A and 54B are inserted and fitted into the second through-holes 53d of the first stoppers 53A and 53B under pressure. With this constitution, when the connection between the first coupling member 80 and the first arm part 20 is released before the connection between the second coupling member 90 and the second arm part 30 is released, the operation wire 40 is further retreated. Thereby, the second transmitting member 52 can be easily pulled to the proximal end side, and the connection between the second coupling member 90 and the second arm part 30 can be easily released.

In the present embodiment, the example in which the first transmitting member 51 is connected to the distal end side of the operation wire 40 has been represented, but the operation wire and the first transmitting member may be integrally configured. That is, the operation wire 40 may be configured to be inserted into and fixed to the first through-hole 53c of the first stopper 53, and the distal end part of the operation wire 40 may be configured to be fixed to the first coupling member 80. In this case, the distal end side of the operation wire 40 which is than the first stopper 53 becomes the first transmitting member.

Second Embodiment

A clip device 1A according to a second embodiment will be described with reference to FIGS. 13 to 20. In the embodiment to be described below, components that are the same as those of the clip device according to the above-mentioned first embodiment in terms of function or structure will be given the same reference signs as in the first embodiment, and description overlapping that of the first embodiment will be omitted.

Figure 13:
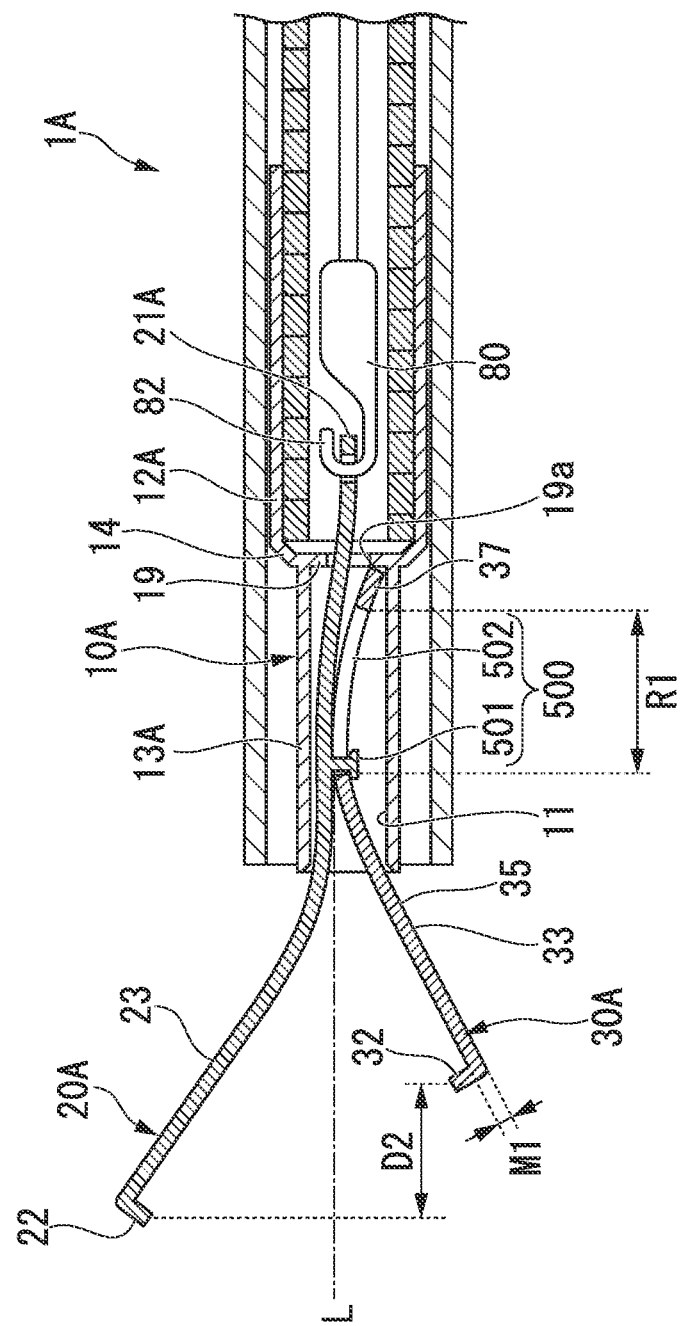
FIG. 13 is a sectional view illustrating a distal end portion of a clip device according to a second embodiment.
Figure 14:
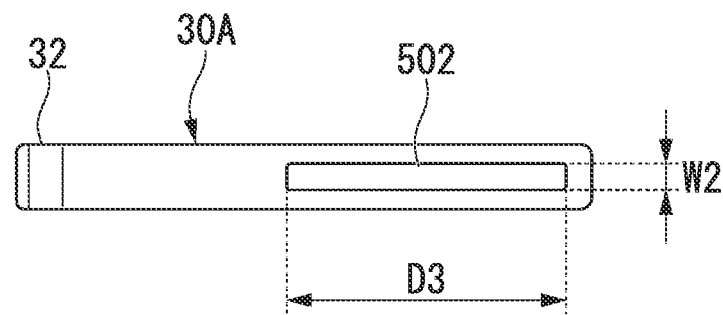
FIG. 14 is a top view illustrating a second arm part in the second embodiment.
Figure 15:
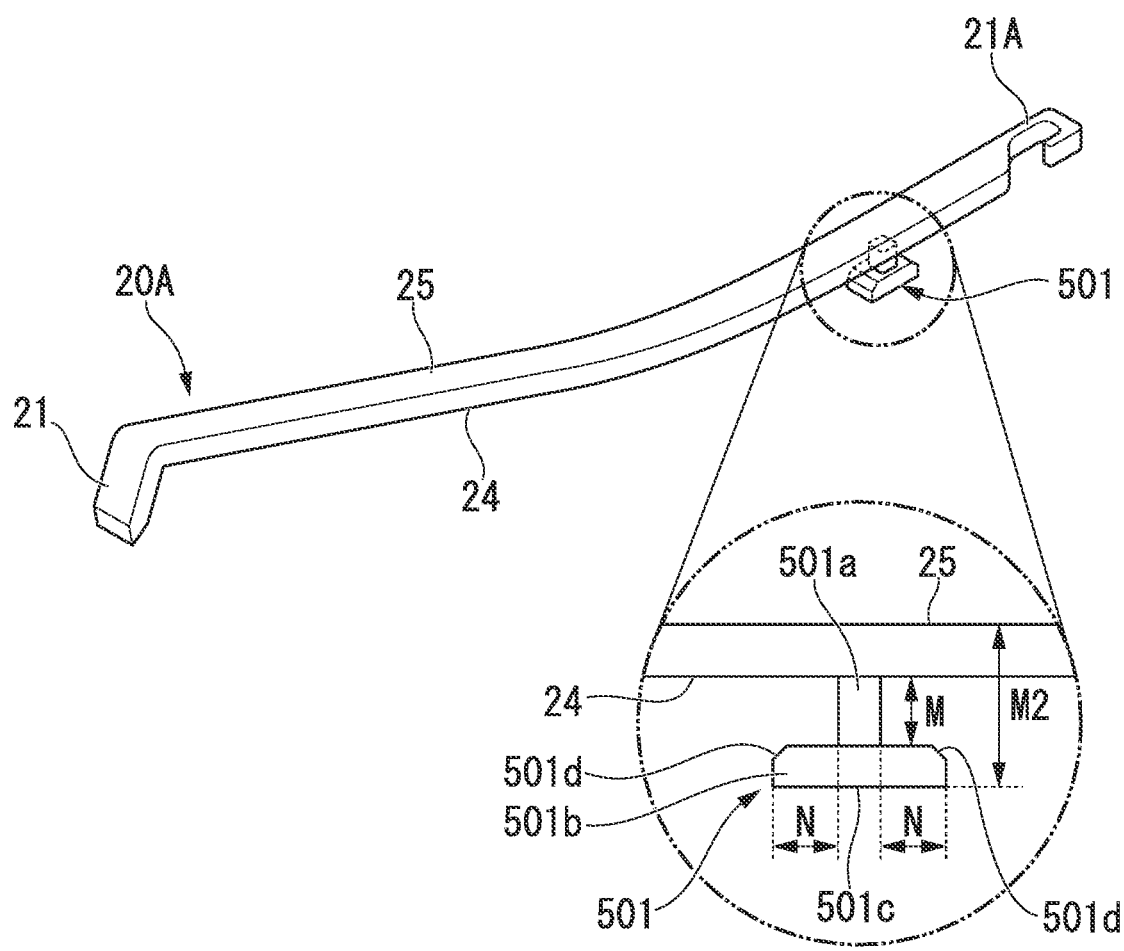
FIG. 15 is a perspective view illustrating a first arm part in the second embodiment.
Figure 16:
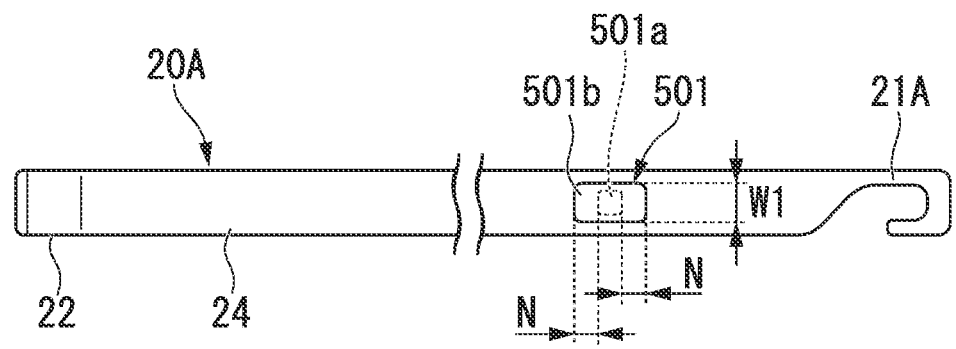
FIG. 16 is a top view illustrating the first arm part in the second embodiment.

In the clip device 1A according to the present embodiment, constitutions of a movement adjusting mechanism, a first arm part, a second arm part, and a restraining tube are different from those of the first embodiment. FIG. 13 is a sectional view illustrating a distal end portion of the clip device 1A. FIG. 14 is a side view of the second arm part viewed from an outer surface 35 side. FIG. 15 is a perspective view illustrating the first arm part 20A of the present embodiment. FIG. 16 is a side view of the first arm part 20A viewed from an inner surface 24 side.

The restraining tube 10A is a tubular member having an insertion passage 11, and has a large diameter part 12A located at the proximal end side thereof and a small diameter part 13A that is disposed at the distal end side thereof and is formed such that a diameter of an opening thereof is smaller than that of the large diameter part 12A. The diameter of the opening of the large diameter part 12A is greater than an outer circumferential surface of a sheath 60. Like the first embodiment, the restraining tube 10A has a tapered part 14 between the large diameter part 12A and the small diameter part 13A. A protrusion part 19 protruding from an inner surface of the insertion passage 11 in a radial direction is formed between a second insertion passage 16 and a third insertion passage 17 in an annular shape in a circumferential direction. An opening 19a of an inner circumference of the protrusion part 19 is open in such a size that the first arm part 20A and a second arm part 30A can be advanced and retreated. The restraining tube 10A is mounted on a distal end of the sheath 60. To be specific, the restraining tube 10A is inserted into a first insertion passage 15 up to a position at which the distal end of the sheath 60 comes into contact with a proximal end of the tapered part 14, and the insertion passage 11 of the restraining tube 101 is disposed to communicate with a lumen 61 of the sheath 60.

The movement adjusting mechanism 500 has a convex part 501 and a slit 502. The movement adjusting mechanism 500 according to the present embodiment is provided for the first arm part 20A and the second arm part 30A. The clip device 1A according to the present embodiment does not have the first transmitting member 51, the second transmitting member 52, the first stopper 53, the second stopper 54, the third stopper 55, and the ring member 57 in the first embodiment.

Figure 17A:
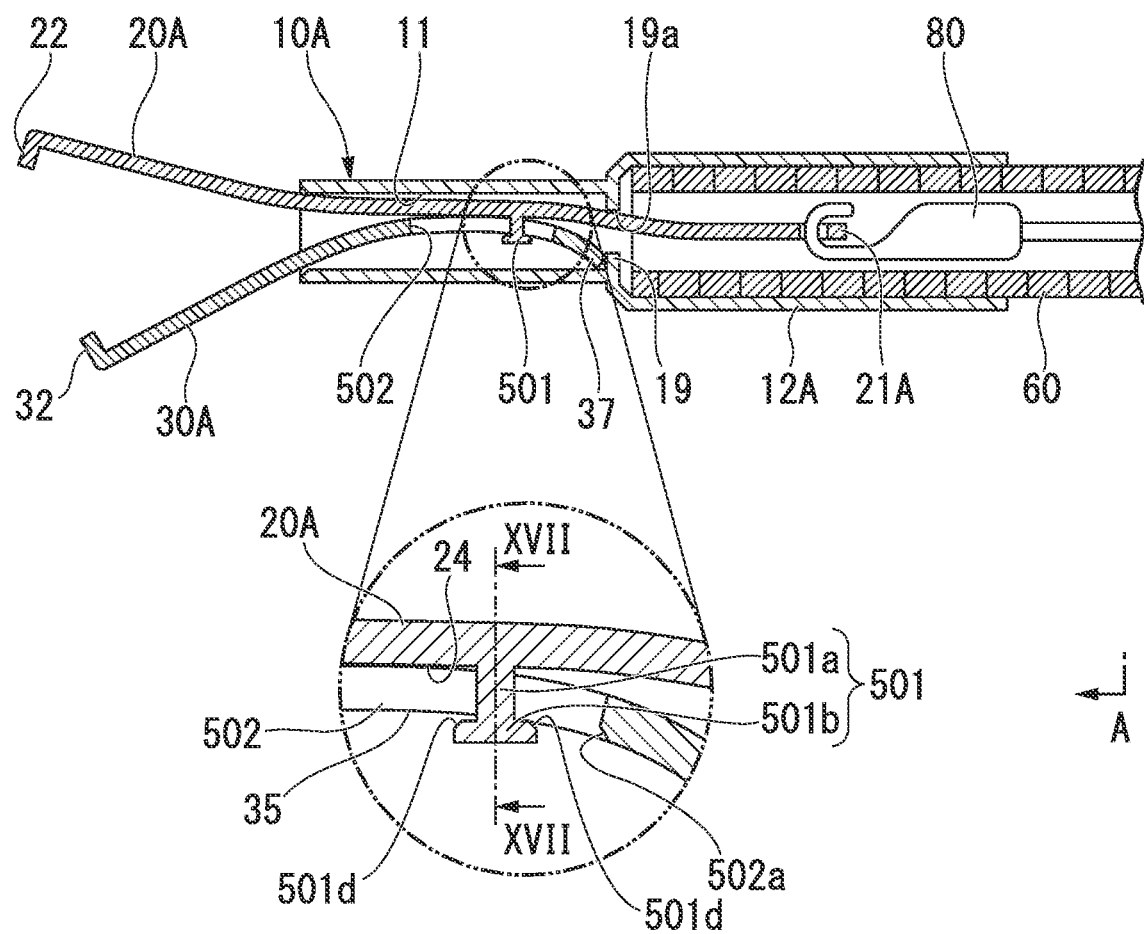
FIG. 17A is a sectional view illustrating the distal end portion of the clip device according to the second embodiment.

As illustrated in FIGS. 13 and 14, the second arm part 30A has a second claw part 32 and the slit 502. The second claw part 32 has the same constitution as in the first embodiment. The slit 502 is formed to extend from a proximal end side of the second arm part 30A to a middle portion in a longitudinal direction. The slit 502 penetrates the second arm part 30A in a plate thickness direction. As illustrated in FIG. 17A, chamfered oblique parts 502a are formed at opposite ends of an edge of an opening of the slit 502 at the outer surface 35 side of the second arm part 30A in a direction of a longitudinal axis L. A second curved part 33 curved like a bow away from the longitudinal axis L of the restraining tube 10A is formed from the distal end to the proximal end of the second arm part 30A. The second curved part 33 is formed to be elastically deformed when an external force acts thereon and to be restored to the curved shape in a natural state in which no external force acts thereon.

The first arm part 20A is provided with a first claw part 22, a first curved part 23, a first engaging part 21A, and the convex part 501. The first engaging part 21A is includes a recess formed by cutting out an end part in a plate width direction in a proximal end of the first arm part 20A. As illustrated in FIGS. 15 and 17A, the convex part 501 is provided to protrude from an inner surface 24 of the first arm part 20A. The convex part 501 has a base part 501a that vertically extends from the inner surface 24 in the plate thickness direction, and a flat plate part 501b that is fixed to the base part 501a and is provided parallel to the inner surface 24.

Figure 17B:
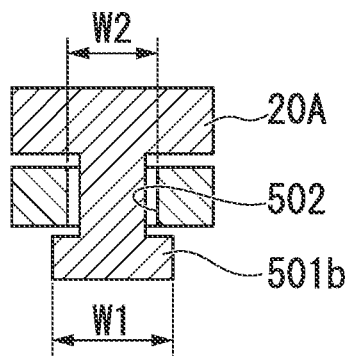
FIG. 17B is a sectional view taken along arrow XVII-XVII of FIG. 17A.

As illustrated in FIGS. 16 and 17B, a size W1 of the flat plate part 501b in the plate thickness direction (in the direction perpendicular to the longitudinal axis L) has a size that is equal to or greater than an opening width W2 in the direction perpendicular to the direction of the longitudinal axis L of the slit 502 illustrated in FIG. 14. A protruding length M of the base part 501a from the inner surface 24 is longer than a plate thickness M1 of the second arm part 30A. In addition, as illustrated in FIG. 15, an amount of protrusion of the convex part 501 from the inner surface 24 is set such that a length M2 from the outer surface 25 of the first arm part 20A to a protruding end face 501c of the flat plate part 501b is smaller than a diameter of the opening 19a of the restraining tube 10A. Sizes N from opposite ends of the flat plate part 501b in the direction of the longitudinal axis L to the base part 501a are set in such a size that a proximal end part and a distal end part of the slit 502 can be engaged. As in the first embodiment, the first arm part 20A is provided such that the first engaging part 21A and the operation wire 40 are connected and the first arm part 20A can be advanced and retreated in the restraining tube 10 depending on the advance and retreat of the operation wire 40. A length of the first arm part 20A in a longitudinal direction is longer than that of the second arm part 30A in a longitudinal direction. As illustrated in FIG. 15, oblique parts 501d are formed at ends of the flat plate part 501b which are close to the inner surface 24 at end faces of the flat plate part 501b in the longitudinal direction.

The movement adjusting mechanism 500 is configured such that the convex part 501 provided for the first arm part 20A is inserted into the slit 502 provided for the second arm part 30A and slides in the slit 502. With this constitution, when the operation wire 40 is operated to retreat by a predetermined amount, a state can be switched in which the second arm part 30A is retreated along with retreat of the first arm part 20A.

Next, a connecting structure of each member of the clip device 1A and an operation of the movement adjusting mechanism 50 will be described. FIG. 13 illustrates an initial state in which the clip device 1A is used.

The restraining tube 10A, the first arm part 20A, and the second arm part 30A are provided to be mountable and demountable on the sheath 60. The restraining tube 10A is disposed to cover an outer circumference of the distal end of the sheath 60, and the first arm part 20A is engaged on a first coupling member 80. Thereby, this disposing relation is maintained.

The first arm part 20A and the second arm part 30A are inserted into the restraining tube 10A at the proximal end sides thereof, and are provided to protrude from the distal end of the restraining tube 10A at the distal end sides thereof. The first arm part 20A is inserted into the restraining tube 10A along with the second arm part 30A in a state in which the convex part 501 is inserted into the slit 502 of the second arm part 30A. In the initial state, the convex part 501 and the slit 502 are disposed inside the third insertion passage 17. The second arm part 30A is disposed such that a proximal end 37 thereof comes into contact with a distal end face 19b of the protrusion part 19, and a movement of the second arm part 30A toward the first insertion passage 15 side of the restraining tube 10A is regulated.

In the initial state illustrated in FIG. 13, a position of the distal end (the first claw part 22) of the first arm part 20A in the direction of the longitudinal axis L is located at the distal end side than a position of the distal end (the second claw part 32) of the second arm part 30A. An opening length D3 (see FIG. 14) of the slit 502 in the longitudinal direction is set to be equal to a distance D2 between the first claw part 22 and the second claw part 32 in the direction of the longitudinal axis L when the first arm part 20A and the second arm part 30A fully protrude from the restraining tube 10A. A position of the slit 502 at the second arm part 30A is set based on a position of the first arm part 20A in the direction of the longitudinal axis L. When the proximal end 37 of the second arm part 30A is engaged by coming into contact with the protrusion part 19, the second arm part 30A is located to fully protrude from the distal end of the restraining tube 10A. When the second arm part 30A fully protrudes from the distal end of the restraining tube 10A and the base part 501a of the convex part 501 comes into contact with the distal end of the slit 502, the positions of the convex part 501 and the slit 502 are set such that the first arm part 20A is located to fully protrude from the distal end of the restraining tube 10A.

As illustrated in FIG. 13, the first coupling member 80 is fixed to the distal end of the operation 40. A first hook part 82 of the first coupling member 80 and the first engaging part 21A are engaged inside the first insertion passage 15. Therefore, depending on the advance and retreat of the operation wire 40 in the sheath 60, the first arm part 20A is configured to be advanceable and retreatable in the restraining tube 10A in the direction of the longitudinal axis L.

Since the operation wire 40 and the first arm part 20A have the connecting structure, the advance and retreat motion of the operation wire 40 is directly transmitted to the first arm part 20A so that the first arm part 20A is advanced and retreated. A relation between the advance and retreat motion of the operation wire 40 and the advance and retreat of the first arm part 20A is maintained in a state in which the first arm part 20A is engaged on the first coupling member 80. Since the proximal end 37 in the second arm part 30A is ed on the protrusion part 19 and the convex part 501 disposed in the slit 502, when the convex part 501 slides in the slit 502 (a first range R1) as illustrated in FIG. 17A, the second arm part 30A does not follow the advance and retreat movement of the first arm part 20A. For this reason, the first arm part 20A is advanced and retreated in the restraining tube 10A independently of the second arm part 30A. When the first arm part 20A retreats in the inside of the restraining tube 10A, the outer surface 25 of the first arm part 20A is elastically deformed to be pressed against an opening part of the distal end of the restraining tube 10A, and the first claw part 22 moves along a locus of the direction inclined with respect to the proximal end side to approach the second claw part 32.

Figure 18:
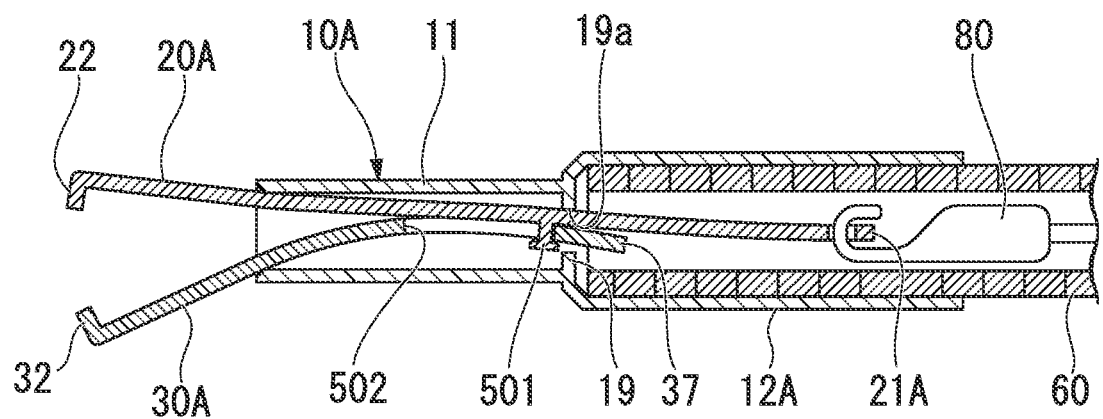
FIG. 18 is a sectional view illustrating the distal end portion of the clip device according to the second embodiment.

When the first arm part 20A independently retreats in the restraining tube 10A and moves to a position at which the base part 501a comes into contact with the proximal end of the slit 502, the first claw part 22 is located around the second claw part 32. When the convex part 501 approaches the proximal end of the slit 502, the oblique part 501d of the flat plate part 501b and the oblique part 502a of the proximal end side of the slit 502 come into contact with each other. Further, when the convex part 501 retreats, the proximal end 37 of the second arm part 30A spaced apart from the first arm part 20A as illustrated in FIG. 18 is engaged between the flat plate part 501b and the inner surface 24 of the first arm part 20A, and moves to the first arm part 20A side. In this case, since the flat plate part 501b and the slit 502 have the dimensional relation illustrated in FIG. 17B, the convex part 501 can be prevented from escaping from the slit 502.

When the operation wire 40 is further pulled to the proximal end side in this state (a second range), the proximal end 37 of the second arm part 30A is pressed against the proximal end side by the convex part 501, and the second transmitting member 52 retreats along with the retreat of the first transmitting member 51. As a result, the second arm part 30 moves (retreats) to the proximal end side in the restraining tube 10. When the first arm part 20A moves to the distal end side in a state in which the convex part 501 is in contact with the distal end of the slit 502, the second arm part 30A can also move to the distal end side as in the first embodiment.

Figure 19:
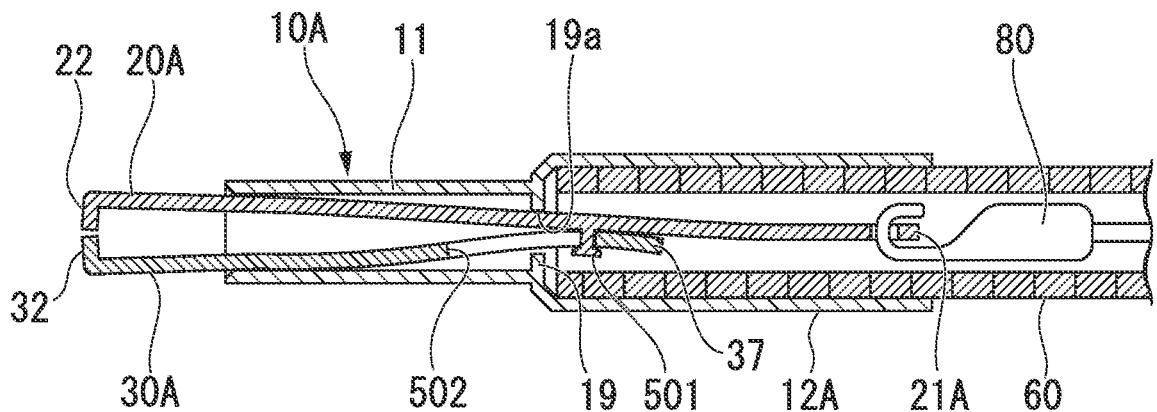
FIG. 19 is a sectional view illustrating the distal end portion of the clip device according to the second embodiment.

When the operation wire 40 is pulled in a second state, the convex part 501 and the proximal end 37 of the second arm part 30A pass through the opening 19a of the protrusion part 19 as illustrated in FIGS. 18 and 19. Then, since the second arm part 30A is pressed against the opening of the distal end of the restraining tube 10A and moves to the proximal end side along with the first arm part 20A, the second claw part 32 is elastically deformed toward the longitudinal axis L, and the first claw part 22 and the second claw part 32 face and come into contact with each other. Here, when the first claw part 22 and the second claw part 32 come into contact with each other on the longitudinal axis L, this is favorable because tissue can be grasped with a higher grasping force. As illustrated in FIG. 19, when the convex part 501 and the proximal end part 37 of the second arm part 30A are disposed inside the first insertion passage 15, the first arm part 20A and the second arm part 30A are pressed by the insertion passage 11 of the restraining tube 10, and a mucous membrane T between the first claw part 22 and the second claw part 32 is more strongly held. An operator can recognize that the convex part 501 and the proximal end part 37 of the second arm part 30A are disposed inside the first insertion passage 15 by a pulled position of a slider 71 from an operation part 70.

Subsequently, even when the operation wire 40 is further pulled in a state in which the mucous membrane T is held by the first arm part 20A and the second arm part 30A, the first arm part 20A and the second arm part 30A do not move because the movement to the proximal end side is regulated by a frictional force between the insertion passage 11 of the restraining tube 10A and the first arm part 20A and between the insertion passage 11 and the second arm part 30A. For this reason, a great load is applied to the first hook part 82 so that the first hook part 82 is subjected to plastic deformation, and the engagement of the first engaging part 21 and the first hook part 82 is released. As a result, the connection between the first transmitting member 51 and the first arm part 20A is released.

Figure 20:
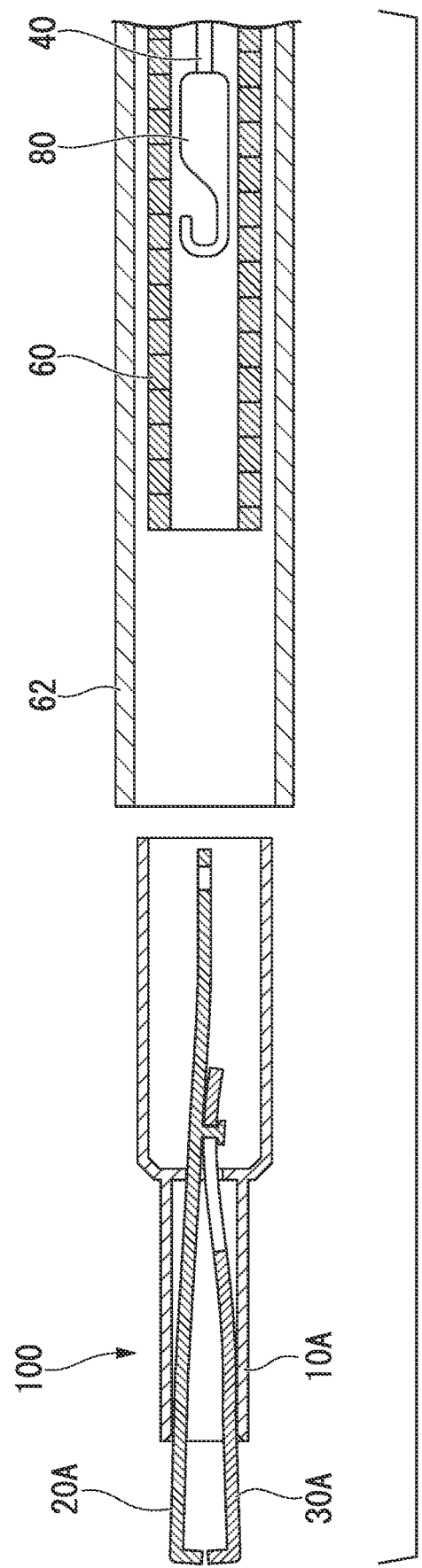
FIG. 20 is a sectional view illustrating the distal end portion of the clip device according to the second embodiment.

When the connection between the operation wire 40 and the first arm part 20A is released, the butting relation between the restraining tube 10 and the sheath 60 is also released. As illustrated in FIG. 20, the restraining tube 10A falls from the sheath 60, and the clip unit 100 ligates the mucous membrane T and is placed. Afterwards, the sheath 60, the operation wire 40, and a coupling member 90 are pulled out from an endoscope insertion part, and the clip device 1A is removed.

According to the present embodiment, like the first embodiment, when the mucous membrane T or the like of the digestive tract is ligated through an endoscope, a process in which the mucous membrane T is pinched and ligated by the first arm part 20A and the second arm part 30A can be smoothly performed. Since the second arm part 30A does not follow a motion in which the first arm part 20A is pulled until the first claw part 22 approaches the second claw part 32, the position of the second arm part 30A with respect to the tissue can be fixed. Therefore, in comparison with a conventional clip unit, the operation of pulling the clip unit 100 to the proximal end side is facilitated while the tissue is pressed. According to the present embodiment, the constitution of the movement adjusting mechanism 500 becomes a simple constitution, and assembly is facilitated.

While embodiments have been described above in detail with reference to the drawings, the specific constitution is not limited to the embodiments, and also includes a change in design or the like without departing from the scope of the disclosed embodiments.

The components represented in the embodiments and the modifications can be configured in appropriate combinations.

In the first embodiment, the example in which the second stopper 54 and the third stopper 55 are provided for the second transmitting member 52 has been represented, but only the second stopper 54 may be configured to be provided for the second transmitting member 52.

In the first embodiment, the example in which the ring member 57 has the communicating holes has been represented. However, in place of the communicating holes of the ring member 57, annular protrusion parts protruding from the inner surface of the lumen 61 of the sheath 60 may be provided, and the restraining tube 10, the third stopper 55, or the first stopper 53 may be configured to conic into contact with the annular protrusion parts.

The example in which the protrusion parts 26 and 36 are provided for the first arm part 20 and the second arm part 30 of the first embodiment and thereby serve as the wedges in the insertion passage 11, and the first arm part 20 and the second arm part 30 are fixed to the restraining tube 10 has been represented, but the protrusion parts 26 and 36 are not necessarily configured. For example, like the second embodiment, the sizes of the first arm part 20 and the insertion passage 11 and the sizes of the second arm part 30 and the insertion passage 11 are adjusted, and thereby the first arm part 20 and the second arm part 30 may be configured to come into contact with the insertion passage 11 under pressure and to be fixed to the restraining tube.

In the second embodiment, the example in which, when moving to the proximal end side to enter into the closed state, the first arm part 20A and the second arm part 30A come into contact with the insertion passage 11 of the restraining tube 10A, and the movement with respect to the restraining tube 10A is regulated has been represented. However, like the first embodiment, the protrusion parts 26 and 36 may be configured to be provided and engaged on the restraining tube.

In the movement adjusting mechanism 50 of the first embodiment, the example in which the second transmitting member 52 is advanced and retreated in the second through-hole 53d of the first stopper 53, and the first stopper 53 comes into contact with the second stopper 54 and the third stopper 55 has been represented, but the constitution of the movement adjusting mechanism is not limited thereto. For example, like the relation between the convex part and the slider of the second embodiment, the member having the slit may be configured to be fixed to the second transmitting member, and the stopper fixed to the first transmitting member may be configured to serve as the convex part and to slide in the slit.

In the movement adjusting mechanism 500 of the second embodiment, the example in which, when the first arm part 20A is pulled in the state in which the oblique part 501d of the flat plate part 501b of the convex part 501 and the oblique part 502a of the slit 502 come into contact with each other, the proximal end part 37 of the second arm part 30A is engaged on the convex part 501 has been represented, but the oblique parts 501d and 502a are not necessarily configured. For example, if the plate thickness of the flat plate part 501b is sufficiently thin, the flat plate part 501b can be advanced between the inner surface of the insertion passage 11 and the outer surface 35 of the second arm part 30A when the convex part approaches the end of the slit 502 in the direction of the longitudinal axis L.

The shapes of the openings of the insertion passages (the first insertion passage, the second insertion passage, and the third insertion passage) of the restraining tube may be shapes in which the first arm part and the second arm part can be advanced and retreated, and may be, for example, circular shapes, elliptical shapes, oval shapes, rectangular shapes, or the like.

The invention claimed is:

1. A clip device comprising:
   a clip portion including a first arm, a second arm and a restraining tube;
   a wire releasably coupled to the clip portion; and
   a slider coupled to the wire and being slidable on a handle, wherein:
   the first arm extends from a first proximal end to a first distal end;
   the second arm extends from a second proximal end to a second distal end;
   the second proximal end is slidably received within the restraining tube so that the second arm is movable between an open configuration, in which the second arm is moved laterally away from the first arm and the second distal end is moved distally relative to the first distal end, and a closed configuration, in which the second arm is moved toward the first arm and the second distal end is moved proximally toward the first distal end;

when the slider is at a distal most position with respect to the handle, the second distal end is disposed distally relative to the first distal end in the open configuration;

in the open configuration, the first arm is configured to move within a first movable range, and the second arm is configured to move within a second movable range; and in a fully open configuration, the first movable range is smaller than the second movable range in a longitudinal direction of the restraining tube.

2. The clip device according to claim 1, wherein:
the handle has an obstruction configured to prevent the slider from moving distally relative to the obstruction in the longitudinal direction of the restraining tube.

3. The clip device according to claim 2, wherein:
the obstruction is a surface of a slit provided along the longitudinal direction of the restraining tube.

4. The clip device according to claim 2, wherein:
in a state that the slider is prevented from moving by the obstruction, the second distal end is arranged distally relative to the first distal end.

5. The clip device according to claim 1, wherein:
the wire is releasably connected to the second arm.

6. The clip device according to claim 1, further comprising:
a sheath in which the wire is capable to being inserted, wherein:
the restraining tube is releasably connected to the sheath.

7. The clip device according to claim 1, wherein:
a first length of the first arm in the longitudinal direction of the restraining tube is smaller than a second length of the second arm in the longitudinal direction of the restraining tube.

8. The clip device according to claim 1, wherein:
the clip device is further configured to change from the closed configuration to a removed configuration, and
in the removed configuration, the first arm is located at the first proximal end within the first movable range, and the second arm is located at the second proximal end within the second movable range.

9. The clip device according to claim 8, wherein:
during a translation from the closed configuration to the removed configuration, both the first arm and the second arm are configured to move proximally.

10. The clip device according to claim 8, wherein:
during a translation from the open configuration to the closed configuration, the second arm is configured to move proximally, and the first arm is configured to maintain a position in the longitudinal direction.

11. A method for treating tissue, comprising:
inserting a clip device, in a closed configuration, to a target area within a living body via a working channel of an endoscope, the clip device including a restraining tube, a first arm and a second arm movably received within the restraining tube;
moving the clip device from the closed configuration to an open configuration in which the second arm is moved laterally away from the first arm and a second distal end is moved distally past a first distal end of the first arm;
in the open configuration, moving the first arm within a first movable range, and moving the second arm within a second movable range, and in a fully open configuration, the first movable range is smaller than a second movable range in a longitudinal direction of the restraining tube;
grasping a first tissue along a first side of the tissue with the first distal end of the first arm;
grasping a second tissue along a second side of the tissue with the second distal end of the second arm, the second side opposing the first side; and
moving the clip device toward the closed configuration, in which the second arm is drawn laterally toward the first arm and the second distal end of the second arm is drawn proximally toward the first distal end of the first arm so that the second tissue is drawn toward the first tissue, thereby closing the tissue.

12. The method for treating tissue according to claim 11, further comprising: locking the clip device in the closed configuration and deploying the clip device.

13. The method for treating tissue according to claim 11, wherein:
the clip device is moved between the open configuration and the closed configuration via an operation wire releasably coupled to a proximal end of the second arm, the operation wire being released from the second arm to deploy the clip device.

14. The method for treating tissue according to claim 11, wherein:
the first distal end of the first arm and the second distal end of the second arm are substantially longitudinally aligned in the closed configuration.

15. The method for treating tissue according to claim 11, wherein:
grasping the second tissue with the second arm in a state that the first tissue is grasped with the first arm.

16. A clip unit comprising:
a clip portion including,
a tube;
a first arm including a first proximal end and a first distal end, and the first arm is configured to move within a first movable range in a longitudinal direction of the tube relative to the tube; and
a second arm including a second proximal end and a second distal end, and the second arm is configured to move within a second movable range in the longitudinal direction relative to the tube, and
wherein the clip portion is configured to be switched between an open configuration and a closed configuration, and
in the open configuration, the first distal end is located at a first distal most end within the first movable range, and the second distal end is located at a second distal most end within the second movable range, and the second distal end is disposed more distally than the first distal end.

17. The clip device according to claim 16, wherein:
the first movable range is smaller than the second movable range in the longitudinal direction.

18. The clip device according to claim 16, wherein:
during a translation from the open configuration to the closed configuration, the second arm is configured to move proximally, and the first arm is configured to maintain a position in the longitudinal direction.

19. The clip device according to claim 16, wherein:
the clip device is further configured to change from the closed configuration to a removed configuration, and
in the removed configuration, the first arm is located at the first proximal end within the first movable range, and the second arm is located at the second proximal end within the second movable range.

20. The clip device according to claim 19, wherein:
during a translation from the closed configuration to the removed configuration, both the first arm and the second arm are configured to move proximally.

* * * * *